(12) United States Patent
Sandhu

(10) Patent No.: US 8,544,309 B2
(45) Date of Patent: Oct. 1, 2013

(54) OSTIAL STENT FLARING APPARATUS

(75) Inventor: Gurpreet S. Sandhu, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 1508 days.

(21) Appl. No.: 12/037,352

(22) Filed: Feb. 26, 2008

(65) Prior Publication Data

US 2008/0208322 A1  Aug. 28, 2008

Related U.S. Application Data

(60) Provisional application No. 60/903,726, filed on Feb. 27, 2007.

(51) Int. Cl.
*B21D 41/02* (2006.01)
*B21D 39/08* (2006.01)

(52) U.S. Cl.
USPC ................ 72/317; 72/370.06; 72/370.1

(58) Field of Classification Search
USPC ............... 72/316–318, 370.03, 370.06, 37.1, 72/370.11, 370.25, 463, 276, 370.1, 370.7
See application file for complete search history.

(56) References Cited

U.S. PATENT DOCUMENTS

| | | | |
|---|---|---|---|
| 3,345,855 A * | 10/1967 | Franck | 72/317 |
| 5,529,349 A * | 6/1996 | Gibbs et al. | 285/332 |
| 5,607,444 A | 3/1997 | Lam | |
| 5,749,890 A | 5/1998 | Shaknovich | |
| 6,125,523 A * | 10/2000 | Brown et al. | 29/516 |
| 7,105,015 B2 | 9/2006 | Goshgarian | |
| 2002/0077691 A1 | 6/2002 | Nachtigall | |
| 2002/0091434 A1 | 7/2002 | Chambers | |
| 2004/0111143 A1 | 6/2004 | Fischell et al. | |
| 2007/0056346 A1 * | 3/2007 | Spenser et al. | 72/402 |

FOREIGN PATENT DOCUMENTS

WO   WO 02/49538 A2   6/2002

* cited by examiner

*Primary Examiner* — Debra Sullivan
(74) *Attorney, Agent, or Firm* — Mueting, Raasch & Gebhardt, P.A.

(57) ABSTRACT

Apparatus, kits and methods for flaring an end of a stent that can then be placed within the ostium of a vessel are disclosed. Areas in which ostial stents with flared ends could be used may include, e.g., the left main artery, renal arteries, subclavian artery, right coronary artery, circumflex artery, et al.

7 Claims, 3 Drawing Sheets

OSTIAL STENT FLARING APPARATUS

RELATED APPLICATIONS

The present application claims the benefit of U.S. Provisional Application No. 60/903,726, titled OSTIAL STENT PREFORMING APPARATUS, KITS AND METHODS, filed on Feb. 27, 2007.

The present invention relates generally to apparatus, kits and methods for modifying stents for ostial placement.

Angioplasty procedures are widely accepted for treatment of occluded arteries, the problem of restenosis following the angioplasty treatment is, however, a complication a patient must face. Restenosis is the reclosure or renarrowing of an artery following trauma caused by angioplasty to open an occluded portion of the artery. Renarrowing is also frequently caused by the elastic rebound of the arterial wall and/or by dissections in the vessel wall caused by the angioplasty procedure. To combat restenosis and maintain the patency of the vessel lumen, physicians implant tubular supports known as stents into surgically repaired vessels.

Stents are used to address restenosis in many patients. The stent is typically inserted by catheter into a vascular lumen at an easily accessible location, such as the brachial or femoral arteries, and then is advanced through the vasculature to the deployment site. The stent is initially maintained in a radially compressed or collapsed state to enable it to be maneuvered through the body lumen, and is mounted to a delivery system for advancement through a patient's vasculature to the deployment site. Once the stent has reached the stenotic site within a damaged vessel, and is ready for deployment, it is expanded by internal means or by means integral to the delivery system that are well known in the prior art. In its expanded state, the stent provides internal support for the vessel lumen and reduces the likelihood of the development of restenosis.

Placement of the stent within the vasculature can be especially challenging when the stenotic region is near the intersection of two vessels or is at the origin of a major vessel off the aorta. For example, the placement of a stent to repair a diseased vessel that is a branch vessel, such as the renal artery, near its ostium with a great vessel, such as the aorta, is particularly challenging because the stent must be securely and precisely positioned in an area that supports a heavy volume of blood flow without occluding the blood flow in either the branch vessel or the great vessel. Additionally, the angle created by the intersection of a main/great vessel and a branch vessel can lead to difficulties in precisely positioning the stent in the damaged branch vessel. Physicians often have difficulty aligning the stent to optimally repair the stenotic region of such a branch vessel, which leads to placement of the stent within the branch vessel such that a portion of the stent hangs out or extends into the main vessel. This can result in partial obstruction of the main vessel and can also make it difficult to reenter the branch vessel for repeat procedures in the future. Attempts to position a stent without any proximal overhang into the main vessel can often lead to the stent being positioned too deep inside the branch vessel, thereby incompletely covering the ostial narrowing.

Conventional stents are designed to repair areas of blood vessels that are generally located somewhere along the length of single elongated vessel, and as such, they are not sufficiently equipped to be reliably and securely placed at a site that has a substantially ostial location at an intersection. Use of such conventional stents in the vicinity of vessel intersections may lead to undesirable shifting of the stent within the vessel and deployment further downstream such that the ostium is left uncovered.

Some stents have incorporated various arrangements to assist in securing the expanded stent to the walls of the vessel lumen in a stenotic region. Examples of such arrangements include rounded protrusions, longitudinal rails, or tines configured to project in some manner from the tubular body of the stent itself and grip into the walls of the vessel lumen. Other designs also have proposed attachments of securing components to the ends of the stent's body, as opposed to the body itself. For example, flaps have been used to assist in securing the stent within a conventional vessel's stenotic region.

Flaring a portion of the stent has been used in the ostium of a bifurcated vessel or a smaller vessel branching off of a larger vessel. Flaring has, however, generally been performed on an ad hoc basis with minimal control over the length and other dimensions of the flared portion of the stent.

SUMMARY OF THE INVENTION

The present invention provides apparatus, kits and methods for flaring an end of a stent that can then be placed within the ostium of a vessel. Areas in which ostial stents with flared ends could be used may include, e.g., the left main artery, renal arteries, sub-clavian artery, right coronary artery, circumflex artery, et al.

In one aspect, the present invention provides an apparatus for flaring a stent, the apparatus including a sterile body having a first end and a second end; a sterile bore formed through the body, the bore having a first opening at the first end and a second opening at the second end, wherein the bore has a first portion proximate the first end and a second portion proximate the second end, wherein the first portion and the second portion meet within the bore, and wherein the first portion has a flared diameter that decreases when moving from the first end towards the second end and the second portion has a substantially constant diameter; and a sterile clamp mechanism located proximate the second opening.

In other aspects, the apparatus may include one or more additional sterile bores formed through the body; wherein each of the additional bores has a first opening at the first end and a second opening at the second end, wherein the additional bore has a first portion proximate the first end and a second portion proximate the second end, wherein the first portion and the second portion meet within the bore, and wherein the first portion has a flared diameter that decreases when moving from the first end towards the second end and the second portion has a substantially constant diameter.

In another aspect, the present invention may provide an apparatus for flaring a stent, the apparatus including a sterile body having a first end and a second end; two or more sterile bores formed through the body, wherein each sterile bore of the two or more sterile bores includes: a first opening at the first end and a second opening at the second end; a first portion proximate the first end and a second portion proximate the second end, wherein the first portion and the second portion meet within the bore, and wherein the first portion comprises a flared diameter that decreases when moving from the first end towards the second end and the second portion comprises a substantially constant diameter; and a sterile clamp mechanism located proximate the second opening.

In various aspects, at least the second portion of the bore may be surrounded by a compression device adapted to compress a stent located within the second portion of the bore. The compression device may include a plurality of segments arranged around the second portion of the bore, an inflatable balloon, etc.

In another aspect, the present invention may provide a kit for flaring the end of an ostial stent, the kit including a sterile expandable stent and a sterile apparatus for flaring an end of the stent. The apparatus may include a body having a first end and a second end; a sterile bore formed through the body, the bore having a first opening at the first end and a second opening at the second end, wherein the bore has a first portion proximate the first end and a second portion proximate the second end, wherein the first portion and the second portion meet within the bore, and wherein the first portion has a flared diameter that decreases when moving from the first end towards the second end and the second portion has a substantially constant diameter; and a sterile clamp mechanism located proximate the second opening of the bore. The kit may further include a sterile expansion device sized for location within the first portion of the bore, wherein the expansion device is capable of flaring the end of the stent outward within the first portion of the bore.

The above summary is not intended to describe each embodiment or every implementation of the present invention. Rather, a more complete understanding of the invention will become apparent and appreciated by reference to the following Description of Exemplary Embodiments and claims in view of the accompanying figures of the drawing.

BRIEF DESCRIPTION OF THE VIEWS OF THE DRAWING

The present invention will be further described with reference to the figures of the drawing, wherein.

DESCRIPTION OF EXEMPLARY EMBODIMENTS

Figure 1:
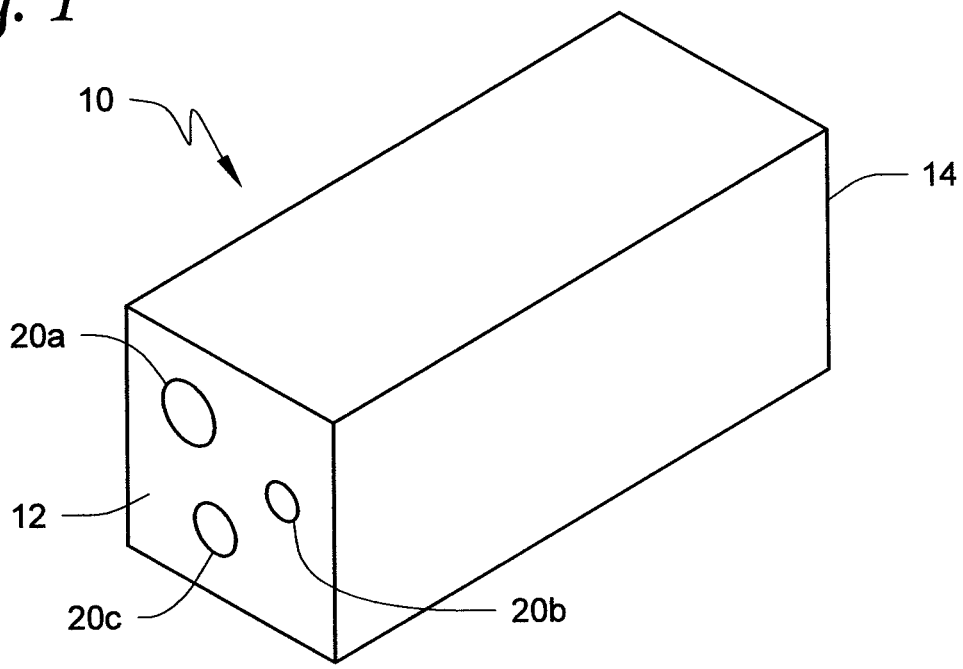
FIG. 1 is a perspective view of one body that includes a plurality of bores formed therethrough.

In the following detailed description of illustrative embodiments of the invention, reference is made to the accompanying figures of the drawing which form a part hereof, and in which are shown, by way of illustration, specific embodiments in which the invention may be practiced. It is to be understood that other embodiments may be utilized and structural changes may be made without departing from the scope of the present invention.

A variety of documents describe the advancement and placement of stents within vessels, including the advancement and placement of ostial stents. See, e.g., U.S. Patent Application Publication Nos. US 2002/0077691 (Nachtigall); US 2002/0091434 (Chambers); US 2004/0111143 (Fischell et al.); etc.—as well as U.S. Pat. No. 5,607,444 (Lam); U.S. Pat. No. 5,749,890 (Shaknovich); etc.

The stents that can be used in connection with the present invention may include, e.g., any conventional stent that can be deformed to include a flared end suitable for ostial placement. In many instances, such stents may be made of metallic materials, although other deformable materials may also be used to manufacture the stents.

FIG. 1 depicts one apparatus that may be used to flare the ends of stents.

The apparatus includes a body 10 having a first end 12 and a second end 14. Bores 20a, 20b, and 20c are depicted as being formed through the body 10. Each of the bores 20a, 20b, and 20c includes a first opening in the first end 12 and a second opening (not shown) in the second end 14 of the body 10.

Although the body 10 is depicted with three bores formed therethrough, the bodies used in connection with the present invention may alternatively include as few as one bore, two bores, or more than three bores.

Figure 2:
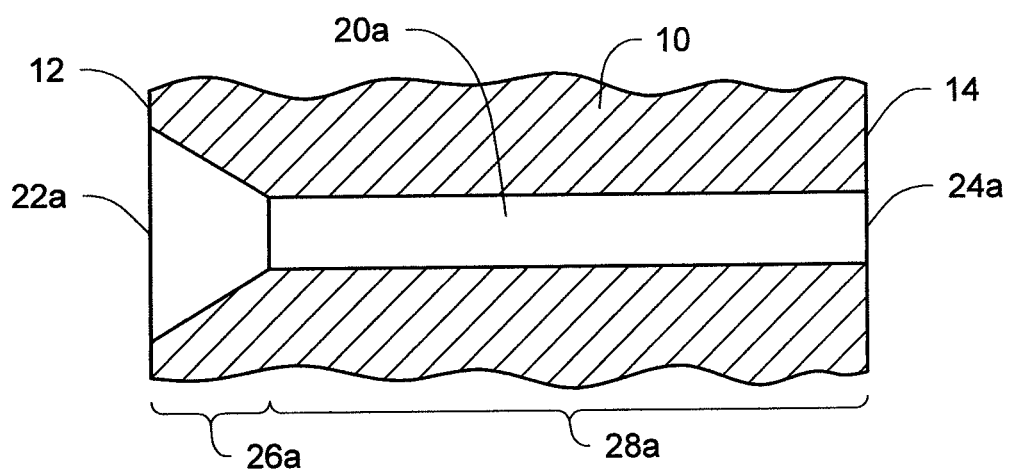
FIG. 2 is a cross-sectional view of one of the bores in the body of FIG. 1.

FIG. 2 is a cross-sectional view of bore 20a. The bore 20a includes a first portion 26a and a second portion 28a. The first portion 26a preferably has a flared diameter that is largest at the opening 22a and decreases when moving from the first end 12 towards the second end 14 of the body 10. The flared shape of the first portion 26a may preferably have a generally circular shape, although other cross-sectional shapes are also possible. Also, although the bore 20a includes a second opening 24a distal from the flared first portion 26a, the bores used in connection with the present invention may alternatively be closed at the distal end.

The first portion 26a of the bore 20a meets the second portion 28a of the bore 20a within the body 10. At the junction between the first portion 26a and the second portion 28a, the diameters of the two portions are preferably equal. While the first portion 26a preferably tapers as depicted in FIG. 2, the second portion 28a may preferably have a substantially constant diameter. In some embodiments, however, the shape of the second portion 28a may differ. For example, the second portion may have a shape that is complementary to a stent to be inserted therein.

It may be preferred that the first portion 26a of the bore 20a be limited to a length of, e.g., less than half of the overall length of the bore 20a between the first end 12 and the second end 14. As an alternative manner of characterizing the length of the flared first portion 26a, it may be preferred that the flared first portion 26a have a length (measured between the first end 12 and the second end 14) of 5 millimeters (mm) or less, or even 2 mm or less.

Figure 3:
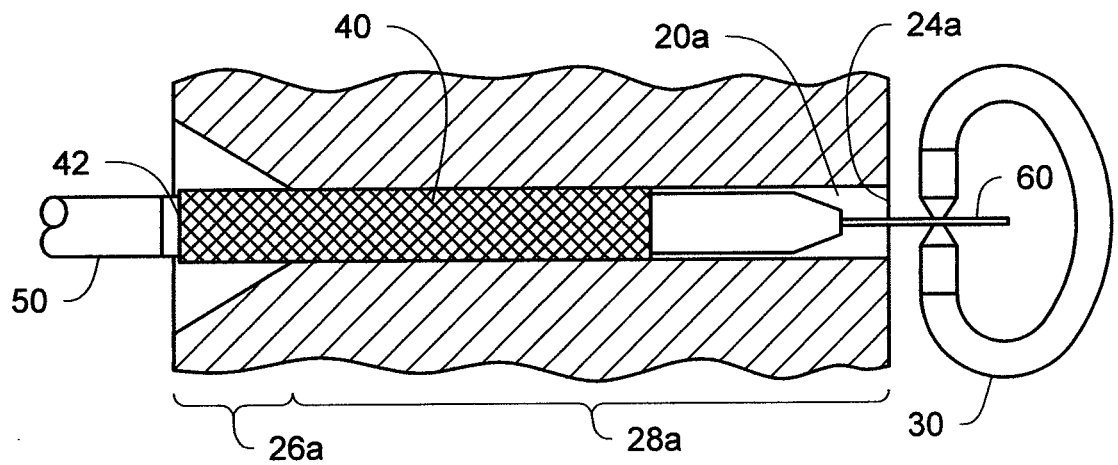
FIG. 3 is a view of FIG. 2 with a stent located therein.

FIG. 3 is a view of the bore 20a of FIG. 2 with a stent 40 located therein. The stent 40 is preferably positioned on a delivery catheter 50, with the catheter 50 located over a guidewire 60. The guidewire 60 may preferably extend out of the distal opening 24a of the bore 20a such that it protrudes from the second end 14 of the body 10 as depicted. When properly positioned, it may be preferred that the proximal end 42 of the stent 40 be generally even with the first end 12 of the body 10.

Also depicted in FIG. 3 is an optional clamp mechanism 30 positioned to retain the guidewire 60 or any other component extending out of the distal end 24a of the bore 20a. It may be preferred that the clamp 30 prevent the guidewire 60 (and associated catheter 50 located thereon) from pulling back into the bore 20a during expansion of the stent 40 to provide a flared end as discussed herein. The clamp 30 may take any form capable of retaining the guidewire 60 in position in the bore 20a by, e.g., compressing the guidewire, etc.

Figure 4:
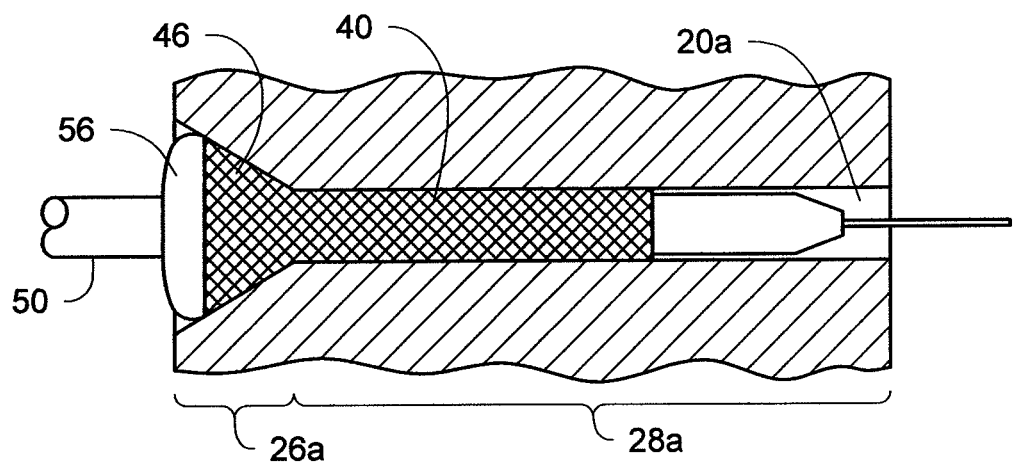
FIG. 4 is a view of FIG. 3 with an expansion device in use to flare the end of the stent within the bore.

FIG. 4 depicts the components of FIG. 3 in which an expandable member 56 (e.g., a balloon, etc.) in the catheter 50 is expanded to force the portion of the stent 40 located within the flared first portion 26a of the bore 20a outwardly to conform to the shape of the flared first portion 26a. It is preferred that the expansion of the stent 40 be such that the proximal end portion 46 of the stent 40 is plastically deformed such that when the stent 40 is deployed within a vessel, the proximal end of the stent 40 exhibits a flared end to assist in retention of the stent 40 in the ostium in which it is deployed.

Although the bores may include first portions that have a flared diameter as described herein, in some apparatus, kits and methods, the bore(s) may not include a flared portion. A stent inserted into a bore that does not include a flared portion may still be flared by leaving a portion of the stent protruding out of the bore, such that expansion of, e.g., a balloon located within the stent, causes the unconstrained portion of the stent (i.e., the portion outside of the bore) to expand and deform into a flared shape. The unconstrained portion of the stent protruding out of the bore may be adjusted by the practitioner to provide the desired flared shape and length.

Figure 5:
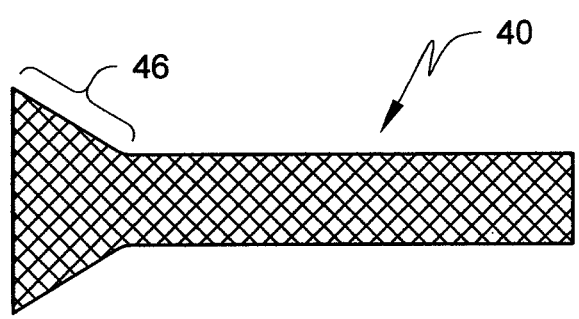
FIG. 5 depicts a stent after flaring.

FIG. 5 depicts the stent 40 outside of the bore. The proximal end portion 46 preferably includes a flared shape that will advantageously promote proper placement and retention of the stent 40 in an ostium. The flared portion of the stent 40 may be reduced in diameter by, e.g., a sheath placed over the stent during delivery to a site. Removal of the sheath before final placement will preferably result in the stent 40 resuming its flared configuration to assist in proper placement and retention. The remainder of the stent 40 may preferably have a uniform diameter (or some other selected shape). The residual flare in the stent 40 after deployment and expansion to its reference size within a vessel is likely to be minimal.

Figure 6:
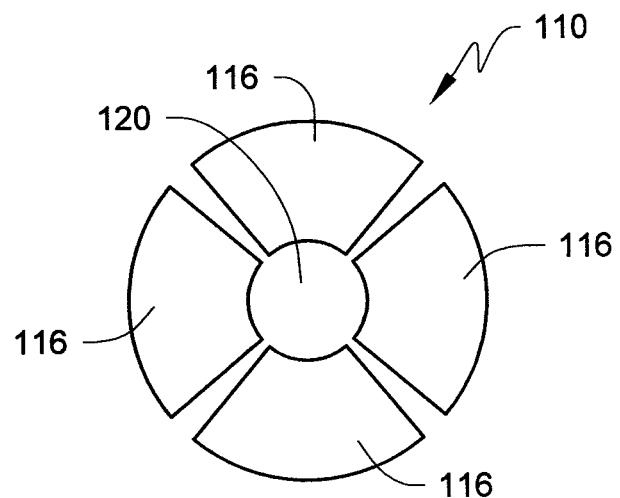
FIG. 6 is a schematic diagram of one alternative design for a body that can be used in connection with the present invention.

FIG. 6 is a schematic diagram of an alternative body 110 in which a bore 120 is located. The body 110 is provided in the form of multiple segments 116 arranged around the bore 120. Although the depicted body 110 includes four such segments 116, it will be understood that it could alternatively include as few as two or three segments or five or more segments. The segments 116 may be provided as one form of a compression device and may preferably be urged towards the center of the bore 120 during use such that the portion of a stent located in the bore 120 can be deformed outwardly to form a flared portion as described herein while the reminder of the stent is compressed to preferably prevent or limit any expansion.

Figure 7:
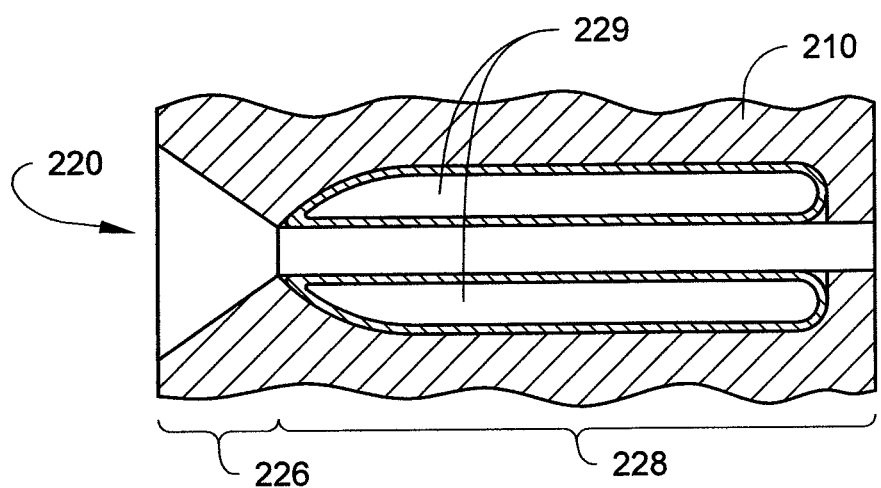
FIG. 7 is a schematic diagram of another alternative design for a body that can be used in connection with the present invention.

FIG. 7 depicts another alternative embodiment of a body 210 in which the second portion 228 of the bore 220 is surrounded by a compression device in the form of one or more balloons 229 (or other expandable member). The first portion 226 of the bore 220 preferably has a flared shape as discussed herein. In use, the balloon within a catheter may be expanded to force the portion of a stent located on the catheter outwardly within the flared first portion 226 to form a flared end on the stent. During such expansion, it may be preferred that the one or more balloons 229 positioned around the remainder of the stent be pressurized such that the portion of the stent located therein is compressed such that it is not expanded.

In a system such as that depicted in FIG. 7, it may be desirable that the pressure within the one or more balloons 229 be greater than the pressure within a balloon used to expand the portion of the stent in the flared first portion 226 of the bore 220. By maintaining such a pressure relationship between the balloon acting on the interior of the stent and the compression device acting on the exterior of the stent, expansion of the balloon located within the stent (which is urging the stent outward) would be contained by the greater pressure of the one or more balloons 229 acting on the exterior of the stent—thus preferably preventing (or severely limiting) expansion of the stent outside of the flared first portion 226 of the bore 220.

It may be preferred that all components of the apparatus and kits used in connection with the present invention be sterile as supplied such that their introduction into a sterile environment does not compromise the sterility of that environment. Sterilization of the components may be accomplished by any suitable technique or combination of techniques.

The terms "comprises" and variations thereof do not have a limiting meaning where these terms appear in the accompanying description and claims. Moreover, "a," "an," "the," "at least one," and "one or more" are used interchangeably herein.

The complete disclosure of the patents, patent documents, and publications cited in the present application are incorporated by reference in their entirety as if each were individually incorporated.

Illustrative embodiments of this invention are discussed and reference has been made to possible variations within the scope of this invention. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

What is claimed is:

1. An apparatus for flaring a stent, the apparatus comprising:
    a sterile body comprising a first end and a second end;
    two or more sterile bores formed through the body, wherein each sterile bore of the two or more sterile bores comprises:
        a first opening at the first end and a second opening at the second end;
    a first portion proximate the first end and a second portion proximate the second end, wherein the first portion and the second portion meet within the bore, and wherein the first portion comprises a flared diameter that decreases when moving from the first end towards the second end and the second portion comprises a substantially constant diameter, wherein, for at least one sterile bore of the two or more sterile bores, at least the second portion of the bore is surrounded by a compression device adapted to compress a stent located within the second portion of the bore, wherein the compression device comprises an inflatable balloon; and
    a sterile clamp mechanism located proximate the second opening.

2. An apparatus according to claim 1, wherein the compression device comprises a plurality of segments arranged around the second portion of the bore.

3. An apparatus according to claim 1, wherein, for at least one sterile bore of the two or more sterile bores, the first portion of the bore is circular in shape.

4. An apparatus for flaring a stent, the apparatus comprising:
    a sterile body comprising a first end and a second end;
    a sterile bore formed through the body, the bore comprising
        a first opening at the first end and a second opening at the second end, wherein the bore comprises a first portion proximate the first end and a second portion proximate the second end, wherein the first portion and the second portion meet within the bore, and wherein the first portion comprises a flared diameter that decreases when moving from the first end towards the second end and the second portion comprises a substantially constant diameter;
    a compression device surrounding the second portion of the bore, wherein the compression device is configured to compress a stent located within the second portion of the bore, wherein the compression device comprises an inflatable balloon; and a sterile clamp mechanism located proximate the second opening.

5. An apparatus according to claim 4, wherein the first portion of the bore extends 5 mm or less into the body from the first end.

6. An apparatus according to claim 4, the apparatus further comprising one or more additional sterile bores formed through the body;

wherein each of the additional bores comprises a first opening at the first end and a second opening at the second end, wherein the additional bore comprises a first portion proximate the first end and a second portion proximate the second end, wherein the first portion and the second portion meet within the bore, and wherein the first portion comprises a flared diameter that decreases when moving from the first end towards the second end and the second portion comprises a substantially constant diameter.

7. An apparatus according to claim 4, wherein the first portion of the bore is circular in shape.

* * * * *